US009222911B2

(12) United States Patent
Liemersdorf et al.

(10) Patent No.: US 9,222,911 B2
(45) Date of Patent: Dec. 29, 2015

(54) METHOD AND DEVICE FOR DETECTING AT LEAST ONE PROPERTY OF A GAS

(75) Inventors: Dirk Liemersdorf, Sachsenheim (DE); Benjamin Sillmann, Moehringen (DE)

(73) Assignee: ROBERT BOSCH GMBH, Stuttgart (DE)

( * ) Notice: Subject to any disclaimer, the term of this patent is extended or adjusted under 35 U.S.C. 154(b) by 298 days.

(21) Appl. No.: 13/820,650

(22) PCT Filed: Jul. 20, 2011

(86) PCT No.: PCT/EP2011/062419
§ 371 (c)(1),
(2), (4) Date: May 17, 2013

(87) PCT Pub. No.: WO2012/028380
PCT Pub. Date: Mar. 8, 2012

(65) Prior Publication Data
US 2013/0220834 A1  Aug. 29, 2013

(30) Foreign Application Priority Data
Sep. 2, 2010   (DE) .......................... 10 2010 040 146

(51) Int. Cl.
*G01N 27/407* (2006.01)
*G01K 13/02* (2006.01)
*G01N 27/406* (2006.01)
*G01N 27/419* (2006.01)

(52) U.S. Cl.
CPC .............. *G01N 27/407* (2013.01); *G01K 13/02* (2013.01); *G01N 27/4065* (2013.01); *G01N 27/419* (2013.01); *G01K 2013/024* (2013.01)

(58) Field of Classification Search
CPC . G01N 27/406; G01N 27/407; G01N 27/419; G05D 23/24; G01K 7/26
See application file for complete search history.

(56) References Cited

U.S. PATENT DOCUMENTS

| 3,871,981 A | * | 3/1975 | Flais et al. ..................... 204/408 |
| 6,136,170 A | * | 10/2000 | Inoue et al. .................... 204/424 |
| 6,939,037 B2 | * | 9/2005 | Junginger et al. ............ 374/144 |
| 2009/0294285 A1 | | 12/2009 | Nair et al. |
| 2009/0308135 A1 | * | 12/2009 | Reinshagen et al. ........... 73/23.2 |
| 2012/0199478 A1 | * | 8/2012 | Sasaki .......................... 204/406 |

FOREIGN PATENT DOCUMENTS

| DE | 44 15 980 | 11/1995 |
| DE | 10 2006 053808 | 5/2008 |
| DE | 10 2008 040314 | 1/2010 |
| EP | 0 695 983 | 2/1996 |
| EP | 0 769 693 | 4/1997 |
| WO | 2010/003826 | 1/2010 |

OTHER PUBLICATIONS

Robert Bosch GmbH : "Sensoren im Kraftfahrzeug" (Automotive Sensors), 2007Edition, pp. 154-159.

* cited by examiner

*Primary Examiner* — Jennifer Dieterle
(74) *Attorney, Agent, or Firm* — Kenyon & Kenyon LLP

(57) ABSTRACT

A method for detecting at least one property of a gas in a measuring gas chamber, in particular for detecting at least one gas component of the gas. The at least one property is determined using at least one electrochemical measuring cell of a sensor element. Temperatures are detected at at least two different locations of the sensor element and used in determining the at least one property.

13 Claims, 2 Drawing Sheets

METHOD AND DEVICE FOR DETECTING AT LEAST ONE PROPERTY OF A GAS

FIELD OF THE INVENTION

The present invention relates to a method and device for detecting at least one property of a gas. In particular, the present invention concern methods and devices that are used for quantitatively and/or qualitatively detecting at least one gas component in a measuring gas chamber.

BACKGROUND INFORMATION

Numerous devices and methods for detecting one or multiple properties of gases in a measuring gas chamber are known from the related art. For example, the gas may be an exhaust gas of an internal combustion engine, in particular in the automotive sector, and the measuring gas chamber may be an exhaust tract, for example. Alternatively or additionally, however, other properties of the gas may be detected, such as any given physical and/or chemical parameters of the gas, or a different type of gas may be involved.

Many of the methods and devices are based on the use of electrochemical sensor elements. In particular, these may be electrochemical sensor elements which are based on the use of one or multiple solid electrolytes, i.e., the use of solid bodies which have ion-conducting properties, for example oxygen ion-conducting properties, at least above a minimum temperature. For example, this may involve zirconium dioxide-based solid electrolytes such as yttrium-stabilized zirconium dioxide (YSZ) and/or scandium-doped zirconium dioxide (ScSZ). These types of sensors may be used, for example, for determining an air ratio of an exhaust gas. Examples of these types of sensors, also referred to as lambda sensors, are discussed in Robert Bosch GmbH: Sensoren im Kraftfahrzeug (Automotive Sensors), 2007 Edition, pages 154-159. The sensors discussed therein may, in principle, also be used within the scope of the present invention and modified according to the present invention. In addition, sensors for determining a nitrogen oxide ($NO_x$) component, for example, may be used. These types of sensors are discussed in EP 0 769 693 A1, DE 10 2008 040 314 A1, or WO 2010/003826 A1, for example. The devices and methods described in these publications may, in principle, also be employed within the scope of the present invention and modified and used according to the present invention.

In practice, for such methods and devices it has been shown that the measured values ascertained with the aid of these methods and devices, for example measured values of a selective detection of one or multiple gas components, may be greatly dependent on the environmental conditions. In particular, the measured values may be a function of disturbance variables and cross sensitivities, which may have an interfering effect in particular for a quantitative, selective detection of one or multiple gas components, for example $O_2$ and/or $NO_x$, with high resolution, in particular for use as on-board diagnostic sensors. To achieve a required detection accuracy (for example, a $NO_x$ detection in the single-digit ppm range), it is therefore necessary in many cases, in addition to the pure sensitivity of the sensor, to likewise minimize one, multiple, or all occurring disturbance variables and cross sensitivities. In particular, a temperature dependency of the sensor signals must be taken into consideration here. Therefore, in the related art the temperature within the sensor element is generally determined, and the temperature is generally regulated to a setpoint temperature. However, there is still tremendous potential for improvement regarding the minimization or consideration of interfering effects, in particular also the temperature effects on the overall sensor element.

SUMMARY OF THE INVENTION

Therefore, a method and a device for detecting at least one property of a gas in a measuring gas chamber are proposed which at least largely avoid the disadvantages of known methods and devices. As stated above, the at least one property of the gas may in principle be any given physically and/or chemically detectable property. In particular, this may involve a detection of at least one gas component of the gas, i.e., a qualitative and/or quantitative detection of this gas component, for example a percentage and/or a partial pressure of this gas component.

In the proposed method, the at least one property is determined using at least one electrochemical measuring cell of a sensor element. An electrochemical measuring cell is understood to mean a measuring cell which utilizes electrochemical properties, i.e., a Nernst cell and/or a pump cell, for example. In particular, the at least one measuring cell may include at least two electrodes, for example at least two Nernst electrodes and/or at least two pump electrodes, and at least one solid electrolyte which connects the at least two electrodes, for example YSZ, ScSZ, and/or other types of solid electrolytes. In this regard, reference may basically be made to all known sensor elements which in principle are also usable within the scope of the present invention.

In addition, the sensor element may have at least one electrochemical temperature measuring cell, in particular two or more temperature measuring cells. A temperature measuring cell is understood to mean an electrochemical cell which, by use of electrochemical properties and/or measuring principles, allows a temperature at the location of the temperature measuring cell to be ascertained. In particular, the temperature measuring cells may once again be Nernst cells and/or pump cells. In principle, each of the temperature measuring cells may accordingly have at least two electrodes and at least one solid electrolyte which connects the electrodes. For example, based on an internal resistance, in particular an electrolyte internal resistance, of the temperature measuring cells, a temperature at the location of the particular temperature measuring cell may be deduced, since the internal resistance is generally highly dependent on the temperature of the temperature measuring cell. The temperature measuring cells may have a configuration that is completely or partly different from the measuring cell which is used for determining the at least one property of the gas.

Thus, the electrodes and/or the solid electrolyte of the temperature measuring cells may be provided separately from the electrodes and/or the solid electrolyte of the measuring cell. Alternatively or additionally, however, one or more of the temperature measuring cells may have components that are completely or partly the same as the measuring cell. For example, one or more of the temperature measuring cells may share at least one electrode with the measuring cell for detecting the property of the gas. Alternatively or additionally, the solid electrolyte of one or more of the temperature measuring cells may have components that are completely or partly the same as the solid electrolyte of the measuring cell. Various embodiments are possible, and are explained in greater detail below within the scope of various exemplary embodiments.

In the proposed method, temperatures, i.e., at least two temperatures, are detected at at least two different locations of the sensor element and are used in determining the at least one property. For this purpose, at least one temperature measuring element, for example, may be provided. For example, this may be the at least one optional temperature measuring cell described above, which is assumed below without limitation of further possible embodiments. For example, the temperatures may thus be temperatures at the location of the particular optional temperature measuring cell. Alternatively or additionally, one or multiple temperatures may be detected with the aid of at least one other type of temperature measuring element. For example, one or multiple temperatures in the form of at least one temperature information property of at least one heating element, for example at least one heating resistor, may be detected and optionally used. These temperatures are used in determining the at least one property. This means that these temperatures are taken into account in any manner in determining the property, for example in addition to the measured variables of the measuring cell, in an evaluation algorithm and/or by regulating the temperature at the location of the measuring cell. Examples are explained in greater detail below.

In general, within the scope of the present invention a "temperature" is understood to mean a parameter and/or a measured value from which a temperature may be directly or indirectly deduced. For example, this may directly involve a temperature on a temperature scale known to those skilled in the art. Alternatively or additionally, however, this temperature may, for example, be a variable or a parameter which correlates with a temperature, for example a simple digital and/or analog measured value which optionally may yet be converted into a temperature. For example, the internal resistance and/or a value which correlates with the internal resistance of a temperature measuring cell may accordingly also be referred to as a "temperature," since, based on this internal resistance, the temperature may be deduced using known relationships between the internal resistance and the temperature. Various embodiments are possible, so that as a whole, the term "temperature" is to be broadly construed within the scope of the present invention, and may possibly, but not exclusively, encompass actual temperatures on common temperature scales such as a temperature in ° C., ° K, ° F., or the like.

The method may be carried out in particular in such a way that a temperature at the location of the measuring cell may be deduced from the temperatures at the at least two different locations, for example at the locations of the temperature measuring cells.

This may be achieved in various ways, for example by using one or multiple known relationships between the temperatures at the at least two different locations and the temperature at the location of the measuring cell. For example, this at least one relationship may be an extrapolation and/or an interpolation with the aid of which the temperature at the location of the measuring cell may be deduced from the at least two temperatures.

The temperature at the location of the measuring cell may be incorporated in various ways into the determination of the at least one property of the gas in the measuring gas chamber. For example, this temperature may be regulated. For example, a regulation to at least one setpoint temperature may be carried out with the aid of at least one heating element and the temperature at the location of the measuring cell and/or one or more of the temperatures detected with the aid of the temperature measuring cells. A setpoint temperature may be understood, for example, to mean a setpoint temperature at the location of the measuring cell. Accordingly, since multiple measuring cells may also be present, multiple setpoint temperatures may also be used. The setpoint temperature may be a fixed temperature value, but in principle may also include a setpoint temperature which is variable over time.

In addition, the method may be carried out in such a way that at least one measured variable is detected with the aid of the measuring cell. For example, the measured variable may be a Nernst voltage and/or a pump current. Alternatively or additionally, however, other types of measured variables are detectable, depending on the measuring principle and/or the property of the gas to be detected. The at least one property of the gas in the measuring gas chamber may then be determined from the at least one measured variable, taking a correction into account, the correction being a function of the temperatures, in particular temperatures at the location of the temperature measuring cells, or of the other types of temperature measuring devices, and/or of a temperature at the location of the measuring cell. Various types of corrections are possible, for example by using other conversions of the measured variable into the property to be detected, and/or by using one or multiple correction functions, for each or multiple different temperatures. These types of embodiments are basically known to those skilled in the art.

Furthermore, the method may be carried out in such a way that at least one regulation is carried out with the aid of at least one heating element and the temperatures, for example the temperatures at the location of the temperature measuring cells. For example, a regulation of at least one temperature of the sensor element to at least one compromise temperature value may be carried out. The compromise temperature value may be selected, for example, in such a way that for multiple locations of the sensor element, which may be for multiple functional cells of the sensor element (for example, one or multiple Nernst cells and/or one or multiple pump cells of the sensor element), in each case at least one predefined deviation from particular setpoint temperatures is not exceeded. As another example, a regulation may be carried out on the measuring cell in which the measurement for determining the property of the gas has the greatest temperature cross sensitivity.

As described above, the temperature measuring cells may be selected in particular from Nernst cells and/or pump cells. The temperature measuring cells may in each case be used individually or in groups in a dual function or multi-function. Thus, for example, at least one of the temperature measuring cells may be used in addition to the function of a temperature measurement for at least one further function. For example, the at least one further function may be the function of a Nernst cell, for example a Nernst cell with the aid of which a Nernst voltage is detected, and, for example, with the aid of which a gas concentration and/or a partial pressure of a gas component in a chamber adjoined by the Nernst cell may be deduced. For example, the Nernst cell may accordingly be a Nernst cell that is configured as a jump sensor. Alternatively or additionally, the at least one further function may also include the function of a pump cell. Thus, the at least one further function may, for example, be a pump function, for example a function with the aid of which a gas component is removed from a chamber in the sensor element in a targeted manner, for example for removing oxygen from a certain chamber of a sensor element, for example a $NO_x$ sensor element. Other types of pump cells may also be used, for example pump cells for the targeted measurement of a partial pressure of oxygen and/or nitrogen oxides. Various embodiments are possible.

However, in yet other embodiments the measurement of the temperatures may be detected in various ways, in particular when the temperature measuring cells have a dual function. For example, one, multiple, or all of the temperatures, in particular temperatures at the location of the temperature measuring cells, may be detected by at least one or more of the following methods:

- an application of current, in particular an active application of current, and/or an application of voltage, to at least one, which may be multiple or even all, temperature measuring cells is/are modulated, which may optionally also be superimposed with a current and/or a voltage that is actively impressed by the measuring function and/or intrinsically formed, and based on a current signal and/or a voltage signal, which may optionally also be superimposed with a current and/or a voltage that is actively impressed by the measuring function and/or intrinsically formed, an internal resistance of the temperature measuring cells is deduced;
- the temperature measuring cells are acted on by current and/or a voltage, which may be achieved by external application and/or also by formation of an intrinsic current and/or an intrinsic voltage, and based on noise of a current signal and/or a voltage signal of the temperature measuring cells, a temperature at the location of the temperature measuring cells is deduced.

An external application is understood to mean an application of the voltage or the current from outside the particular cell that is acted on, for example via appropriate feed lines, terminal contacts, or similar elements. An intrinsic application is understood to mean that the voltage or the current is generated within the cell itself that is acted on, for example by electrochemical means and/or by reduction of excess charges. Generation of the voltage or the current by other elements of the sensor element is also intended to be subsumable under an intrinsic application. An external as well as an internal or intrinsic application is conceivable. A combination of the mentioned options is also conceivable.

A combination of the above-mentioned methods for temperature determination is also conceivable in principle. Thus, for example, one of the temperature measuring cells may be operated using the first-mentioned option, and at least one additional temperature measuring cell may be operated using the second-mentioned option.

As described above, the method may be used in particular for determining a proportion of at least one of the following gas components in the gas: oxygen; nitrogen oxides; hydrocarbons; hydrogen; ammonia. In particular, these gas components may be detected selectively, quantitatively, and/or qualitatively.

In addition to the proposed method in one or more of the above-described variants, a device for detecting at least one property of a gas in a measuring gas chamber is proposed. The device includes at least one sensor element having at least one electrochemical measuring cell. The sensor element is configured to detect at least two temperatures at at least two different locations of the sensor element. This may once again be achieved, for example, with the aid of at least one, which may be at least two, temperature measuring cell(s), or alternatively or additionally, with the aid of at least one other type of temperature measuring device. With regard to the configuration of the sensor element, reference may be made to the above description and the optional features of the sensor element described there. Moreover, the device includes at least one control system which is configured to carry out a method in one or more of the above-described embodiments. This control system may, for example, be completely or partially integrated into the at least one sensor element. Alternatively or additionally, however, this control system may be completely or partially separate from the at least one sensor element, and connected to the at least one sensor element. For carrying out the at least one method, for example, the at least one control system may include at least one data processing device and/or at least one electronic circuit for carrying out the method. For example, the control system may include at least one microcontroller or some other type of data processing device, optionally having one or multiple volatile and/or nonvolatile memory chip(s). In this way, for example, the method for determining the at least one property may be carried out taking the temperature or temperatures into account by computer, for example with the aid of one or multiple appropriate software module(s). However, other embodiments are also possible in principle.

The proposed method and the proposed device have numerous advantages over known methods and devices. In particular, due to the stated temperature dependency of sensor signals, an exact setting and/or regulation of the temperature is/are possible using the above-described procedure. In contrast to the related art, the temperature is not determined just at one location in the sensor element. It may thus also be taken into account that the actual gas measurement or other type of measurement is generally not carried out in the immediate proximity of the temperature measuring point. In the related art, this disadvantage results in the occurrence of a noncorrectable distortion of the sensor signal when, for example, there is a change in heat dissipation (for example, due to a change in the local gas flow circulation, a change in temperature of the exhaust gas, a change in temperature of the wall of the exhaust gas system, or the like). In contrast to the related art, however, in the method according to the present invention and in the device according to the present invention, an expanded temperature measurement and optionally an expanded temperature regulation are implemented, which, optionally in addition to the temperature measurement at a location in the sensor element, may generate additional information concerning the temperature distribution in the overall sensor element. With the aid of this information and optionally an intelligent heating control system and/or compensation computations which are now possible, a significant improvement in the accuracy of the gas sensor is achievable.

The device according to the present invention and the method according to the present invention allow in particular the use as an on-board diagnostic sensor for the upcoming exhaust gas legislation. This legislation may prescribe nitrogen oxide limiting values which are below the resolution limit of currently available solid electrolyte gas sensors, for example known $NO_x$ sensors.

Exemplary embodiments of the present invention are illustrated in the figures and explained in greater detail in the following description.

DETAILED DESCRIPTION

Figure 1:
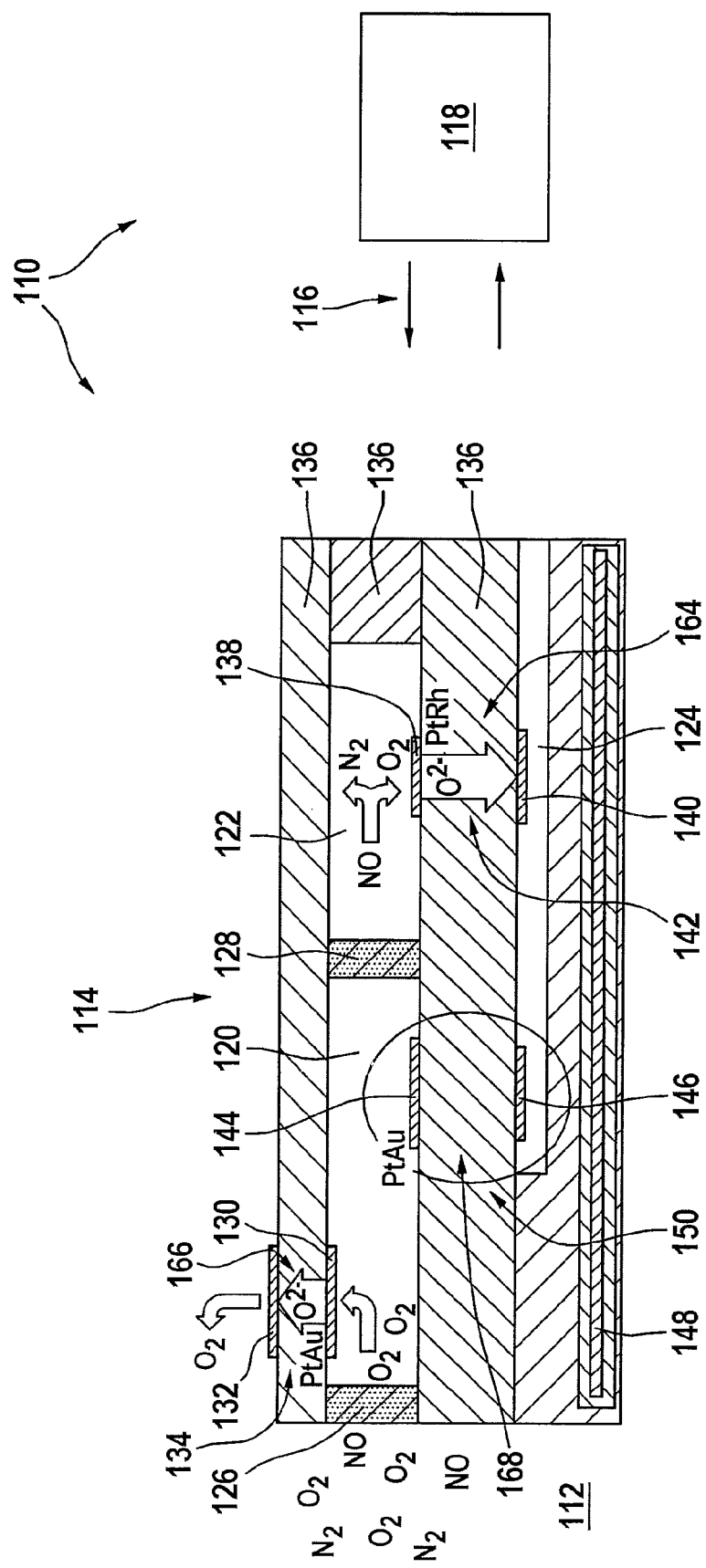
FIG. 1 shows one exemplary embodiment of a device according to the present invention.

FIG. 1 illustrates one exemplary embodiment of a device 110 according to the present invention for detecting at least one property of a gas in a measuring gas chamber 112. Measuring gas chamber 112 may, for example, be an exhaust tract of an internal combustion engine, and the gas may be an exhaust gas of the internal combustion engine. In the illustrated exemplary embodiment, device 110 includes a sensor element 114 and a control system 118 which is connected to sensor element 114 via at least one interface 116. However, in a departure from the illustrated exemplary embodiment, control system 118 may alternatively or additionally be completely or partially integrated into sensor element 114.

In the illustrated exemplary embodiment, sensor element 114 includes a first chamber 120 and a second chamber 122 as well as an air reference 124. First chamber 120 is connected to measuring gas chamber 112 via a first diffusion barrier 126, and second chamber 122 is connected to first chamber 120 via a second diffusion barrier 128. An internal oxygen pump electrode 130 which is made of an electrode material having a low catalytic activity, for example in the form of a platinum-gold cermet, is situated inside first chamber 120. The internal oxygen pump electrode, together with an external oxygen pump electrode 132 situated on the exterior of sensor element 114 and a solid electrolyte 136 which connects electrodes 130 and 132, forms an oxygen pump cell 134. In addition, in the illustrated exemplary embodiment a further internal electrode 144 is provided inside first chamber 120 which cooperates with a reference electrode 146 situated in air reference 124. In the illustrated exemplary embodiment, sensor element 114 also has an NO pump electrode 138 in second chamber 122, which together with a reference pump electrode situated in air reference 124 and a solid electrolyte 136 connecting these electrodes 138, 140 forms an NO pump cell 142. Electrodes 140 and 146 may, for example, also be configured as an electrode which covers both functions. In the exemplary embodiment illustrated in FIG. 1, sensor element 114 also has a heating element 148.

Sensor element 114 illustrated in FIG. 1 is usually used for measuring small gas concentrations of non-oxygen gases, primarily $NO_x$, and to a lesser extent, oxygen that is present. According to this sensor principle, which is known from EP 0 769 693 A1, for example, oxygen in first chamber 120 and optionally in additional prechambers is removed, at least for the most part, from the exhaust gas flowing through first diffusion barrier 126 by pumping out via oxygen pump cell 134 and optionally further oxygen pump cells. Thus, oxygen is ideally subsequently no longer present in second chamber 122. NO pump electrode 138, which in contrast to electrodes 130 and 144 may be made of a catalytically active material (a platinum-rhodium cermet, for example), now decomposes the nitrogen oxides and pumps the oxygen resulting therefrom as ionic current, for example to reference pump electrode 140. The corresponding very small electrical current, whose current intensity at low $NO_x$ concentrations is typically in the nanoampere to microampere range, is measured, and is a measure for the NO or $NO_x$ concentration in the exhaust gas. Reference may be made to EP 0 769 693 A1 for further details of this measuring principle.

To achieve a sufficient ion conductivity of the solid electrolyte, sensor element 114 must generally be heated to a temperature between 600° C. and 900° C. This is achieved with the aid of heating element 148. Since the sensor signals are a function of the temperature, regulation of the temperature is necessary. Customarily, this is generally achieved by measuring the frequency-dependent resistance (electrolyte resistance) of a reference cell which is formed by electrodes 144, 146 and solid electrolyte 136. This area of the temperature measurement according to the related art is symbolically denoted by reference numeral 150 in FIG. 1. Thus, the temperature that is present in this area of sensor element 114 may be deduced based on a known temperature dependency of the electrolyte resistance.

Figure 2:
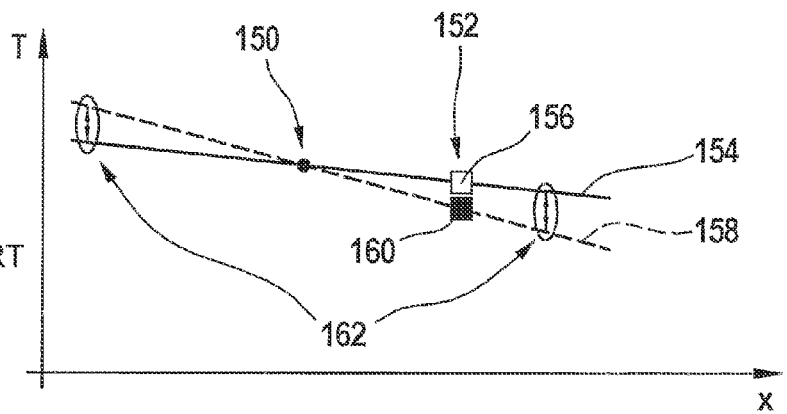
FIG. 2 shows a known method for temperature compensation from the related art.

Due to a given temperature dependency of the sensor signals, in many cases the exact setting and/or regulation of the temperature is an important influencing factor. In the related art, the temperature according to FIG. 1 is determined at only one location in sensor element 114. However, since the actual measurement, for example the nitrogen oxide measurement at NO pump electrode 138, is not carried out in the immediate proximity of the measuring point, distortion of the sensor signal occurs when, for example, there is a change in heat dissipation, for example due to a change in the local gas flow circulation, a change in temperature of the exhaust gas, a change in temperature of the tube wall of the exhaust gas system, or the like. This is illustrated in FIG. 2, which shows a conventional measuring principle having an individual temperature measurement in area 150 according to the configuration in FIG. 1. Temperature T is plotted in FIG. 2 as a function of a location x along an axis of longitudinal extension of sensor element 114. The measuring point of the temperature measurement is once again denoted by reference numeral 150 in FIG. 2, whereas the location of the electrochemical measuring cell, in the present case NO pump cell 142, is denoted by reference numeral 152 in FIG. 2. The temperature regulation is typically carried out on the basis of an assumed temperature gradient 154. An assumed temperature 156 at the location of measuring cell 142 is ascertained on this basis. However, an actual temperature gradient 158 results due to the above-described effects of a change in the heat dissipation, for example due to a change in the local gas flow circulation, a change in temperature of the exhaust gas, a change in temperature of the tube wall of the exhaust gas system, or similar effects. The deviation of this actual temperature gradient 158 from assumed standard temperature gradient 154 is denoted by reference numeral 162 in FIG. 2. This deviation 162 is caused, for example, by different and/or heterogeneous flow circulation and/or a heterogeneous heater. This results in an actual temperature 160 which differs from assumed temperature 156. Due to the generally very small NO measured current, in particular the measurement of the NO signal contains a very high temperature-related error rate as a result of the parasitic electronic leakage current, which varies exponentially with the temperature. Since the further temperature distribution in the sensor element or the temperature gradient is generally not known, in conventional methods and devices it is not possible to compensate for this signal distortion.

In contrast, in the method according to the present invention, devices 110 are used which, in addition to a measuring cell 164, have two temperature measuring cells 166, 168, or in which cells that are already present, for example Nernst cells and/or pump cells, are also used as temperature measuring cells 166, 168 in addition to the original function. Temperatures may thus be determined at at least two different locations of sensor element 114. In the exemplary embodiment according to FIG. 1, oxygen pump cell 134, for example, may also be used as a temperature measuring cell 166 in addition to temperature measuring cell 168 that is already present. Alternatively or additionally, actual measuring cell 164, in the present exemplary embodiment NO pump cell 142, may additionally be a component, in whole or in part, of a temperature measuring cell 166, 168.

The additional knowledge, obtained according to the present invention, of the temperatures at at least two temperature measuring points 170, 172 (whereby a measuring point may analogously also be understood to mean a more extensive area of the sensor element) may be used in various ways. This is illustrated as an example in FIGS. 3 and 4; the methods according to the present invention illustrated there may also be combined.

Figure 3:
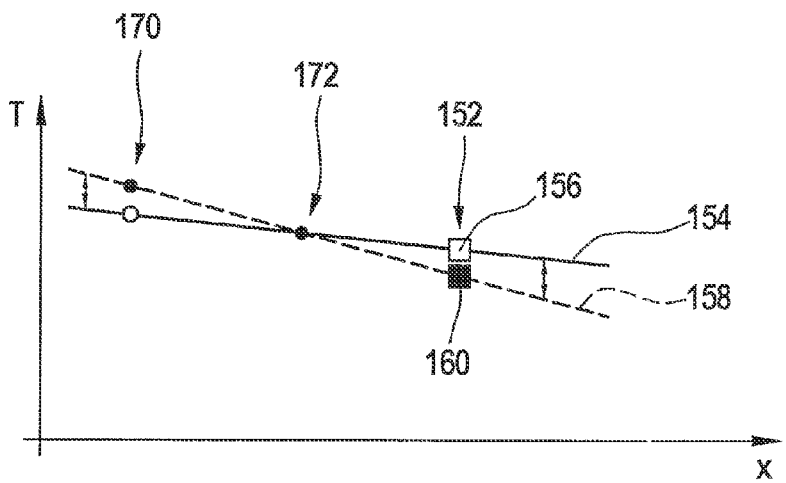
FIG. 3 shows a method according to the present invention for temperature compensation.

Thus, for example, as illustrated in FIG. 3, actual temperature 160 at location 152 of measuring cell 164 may be determined by ascertaining actual temperature gradient 158 with the aid of the actual temperature measurements at measuring points 170, 172, for example by an extrapolation and/or interpolation using actual temperature gradient 158. More complex extrapolation and/or interpolation algorithms are also conceivable. This actual temperature 160 may be used, for example, to convert the pump current of measuring cell 164 into a $NO_x$ concentration and/or a $NO_x$ partial pressure, and/or an evaluation may be provided with appropriate correction factors and/or correction functions.

Figure 4:
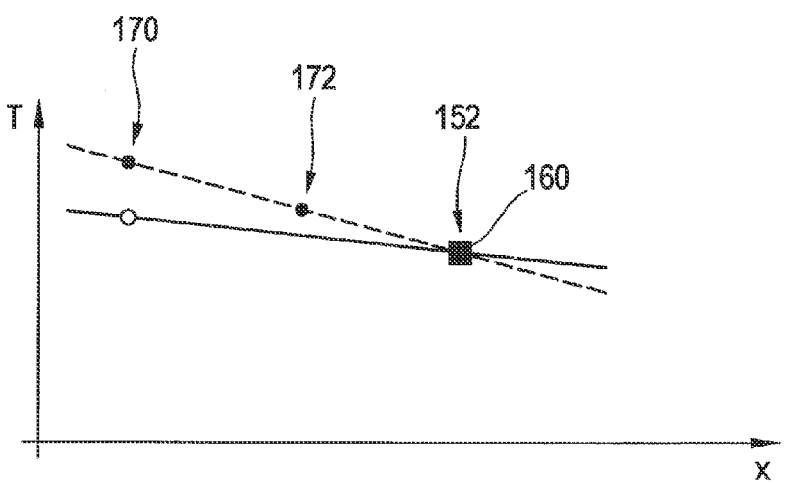
FIG. 4 shows another method according to the present invention for temperature compensation.

Alternatively or additionally, a regulation to a setpoint temperature at location 152 of measuring cell 164 may also be carried out, as illustrated in FIG. 4. In this regard, heating element 148, for example, may be regulated with the aid of a regulator contained in control system 118, for example, using the signals of temperature measuring cells 166, 168 and actual temperature 160 at location 152 of measuring cell 164, in such a way that measuring cell 164 reaches a setpoint temperature.

It is pointed out that the illustrated configuration of device 110 is to be understood solely as an example, and in particular sensor element 114 may be configured in many different ways. In particular, sensor elements 114, for example, may also be used in which second electrode 140 of NO pump cell 142 is situated not in an air reference 124, but, rather, in a gas-tight chamber, i.e., a chamber which is either closed off in a completely gas-tight manner, or which only allows subsequent flow or subsequent diffusion of gas on a time scale which is negligible compared to time scales of customary measurements by sensor elements 114. Examples of these types of sensor elements are described in WO 2010/003826 A1 or in DE 10 2008 040 314 A1. In principle, sensor elements 114 and measuring methods described therein may also be used within the scope of the present invention; however, according to the present invention, temperatures are detected at at least two temperature measuring points 168, 170.

For example, sensor element 114 may have a gas-tight chamber, for example (for example, a cavity or a chamber filled with a porous material) which is separated from the exhaust gas by solid electrolyte 136, for example YSZ. Oxygen may be pumped into the closed chamber between NO pump electrode 138 and a first electrode situated in this gas-tight hollow chamber. At least one third electrode is present in a reference channel or another reference gas chamber, which is connected to the surrounding ambient air, for example (containing approximately 21% oxygen). Depending on the specific embodiment, a further electrode is optionally present in the closed chamber. Depending on the configuration, this further electrode may be combined with the first hollow chamber electrode, or the functionality of the two electrodes may be replaced by a single hollow chamber electrode, thus allowing the number of electrodes to be minimized. To achieve sufficient ion conductivity of the solid electrolyte, the sensor element is generally set to the appropriate operating temperature using an internal heater. The external NO pump electrode catalytically decomposes the gas species to be detected (NO and/or $NO_2$, for example), and corresponding to same, pumps the oxygen thus generated into the gas-tight chamber. This may be implemented either by an active pumping process (for example, by impressing a voltage and/or current function), or in a passive manner by loading the pump cell via an ohmic resistance (so-called autonomous pump cell). For the quantitative determination of the gas species to be detected ($NO_x$, etc.), selectively pumping electrode materials may also be used, and/or the selectivity is supported by an electrochemically assisting pumping process (for example, characteristic decomposition voltage of oxygen-containing gases). In addition, similarly as in FIG. 1, in at least one upstream diffusion-limited chamber the oxygen contained in the exhaust gas may be removed with the aid of a selective oxygen pump cell (having a lower catalytic activity, for example Au—Pt electrodes). Furthermore, cascaded oxygen removal, for example, may optionally be carried out. The various chambers of sensor elements 114 may, for example, be horizontally or also vertically oriented. In addition, the number of electrodes may be reduced by combining multiple electrodes.

In the above-described sensor element 114 (not illustrated) having an additional gas-tight chamber in which at least one of the electrodes of measuring cell 164 is situated, a measuring method, described below, for example, may be applied which is basically known from the related art, for example from the publications WO 2010/003826 A1 or DE 10 2008 040 314 A1 described above. Thus, a quantity of oxygen which correlates with the $NO_x$ concentration may be collected in the gas-tight chamber which is separated from the exhaust gas, using a pumping process (for example, actively with the aid of a pump voltage and/or passively with the aid of an autonomous pump cell). This chamber may be pumped out prior to each new cycle. As soon as an accumulation process begins, oxygen is transported into this gas-tight chamber in correlation with the $NO_x$ concentration and accumulates in this gas-tight chamber. The measuring principle may be subdivided into two phases, for example. In a first phase, for example the gas-tight chamber, which may also be referred to as an accumulation chamber, may be pumped out via a voltage- or current-regulated pumping process, for example, via at least one of the hollow chamber electrodes, the gas-tight chamber being pumped out into an air reference channel, for example. A defined initial state may be established in this way. An associated measured variable of the chamber state may, for example, be a Nernst voltage between a hollow chamber electrode and an electrode situated in the air reference. In a second measuring phase, the oxygen obtained from the NO decomposition and which correlates with the $NO_x$ concentration may be pumped into the accumulation chamber by applying a pump voltage and/or a pump current. As a result, the oxygen concentration in the accumulation chamber increases. The chamber state may be evaluated, for example, by measuring the Nernst voltage between a hollow chamber electrode and a reference electrode, for example an air reference electrode, which is correlated with the oxygen content in the accumulation chamber. In this case, the cell formed from the hollow chamber electrode and the reference electrode would be the actual measuring cell. The measured variable may be, for example, period of time $\Delta t$ required to reach a defined threshold value of the Nernst voltage, which drops with increasing oxygen concentration. With increasing $NO_x$ concentration the accumulation chamber is filled more rapidly, resulting in a quicker drop in the voltage between the hollow chamber electrode and the air reference electrode. However, other evaluation methods for evaluating the chamber state are possible in principle, for example methods in which the Nernst voltage or its variation over time is evaluated in some other way.

These alternative measuring methods and alternative configurations of possible sensor elements 114 are intended to show, solely as an example, that the method according to the present invention and device 110 according to the present invention are transferable to numerous known devices and methods. In addition, the configuration of sensor element 114 illustrated in FIG. 1 is modifiable in various ways. For example, external oxygen pump electrode 132 may be enlarged in terms of its surface area, and internal electrode 144 may be shifted upwardly on the side of solid electrolyte 136 opposite from external oxygen pump electrode 132, so that the two electrodes 130, 144 are situated at the ceiling of first chamber 120. Alternatively or additionally, further electrodes may be situated inside one or more of chambers 120, 122. Once again alternatively or additionally, temperature measuring cells 166, 168 (whereby even further temperature measuring cells may be provided) may be configured in some other way, for example by combining remotely situated electrodes. For example, internal oxygen pump electrode 130 may be combined with reference pump electrode 140 to form a temperature measuring cell, since these electrodes 130, 140 are also connected to one another via solid electrolyte 136.

In the method according to the present invention, in addition to the originally planned function, one or multiple cells may also be used as temperature measuring cells 166, 168 in a dual function. For example, for this purpose one or multiple cells of sensor element 114 may be used which are passive with regard to the sensor signal, i.e., which are not operated in an active manner by impressing current and/or voltage, but, rather, implement a measuring function only in a passive manner (a passive voltage measurement, for example) or do not represent a direct measuring function alone. For example, a temperature measurement may also be carried out via a temperature dependency of electrolyte resistance $R_i$ at active pump cells. For example, one measurement may be carried out at one of oxygen pump electrodes 130, 132 and/or at an oxygen pump cell 134. For this purpose, for example, a signal for the temperature measurement may be superimposed on the regulated pump voltage. For example, a sequence that is sinusoidal and/or triangular and/or configured in some other way, for example a periodic sequence and/or pulses, present in the characteristic range of the cell impedance determined only by the electrolyte resistance, or other temperature-dependent impedances of the cell, may be superimposed on the regulated pump voltage. This may occur at oxygen pump cell 134, for example. To prevent adjustment of these superimposed signal components by the pump voltage controller or pump current controller which is generally used, the associated control variable may be filtered by a low pass filter prior to input into the controller. Internal resistance $R_i$ may then be determined from the likewise suitably filtered (high-pass filtered, for example) current signal, which is to be associated with the targeted excitation. Due to the high frequency of the superimposed low-level signal, the actual pumping operation of the cell is not significantly influenced, and continues to run practically unaffected. This procedure for ascertaining the temperature is likewise possible when a digital method of operating the pump cell is used, for example by utilizing a pulse impression of a digital operating method. In addition, depending on the properties of device 110, it is possible to determine internal resistance $R_i$, without targeted impression of a signal, solely from the superimposed noise components of the pump voltage and/or the pump current, for example due to changes in manipulated variables by the controller, oxygen fluctuations in the exhaust gas, or other sources of noise, and from the associated pump current and/or pump voltage, with appropriate filtering or more complex evaluation methods.

With the aid of the described method, as an alternative or in addition to the use of at least one Nernst cell for temperature measurement it is thus possible, for example, to use at least one, multiple, or even all pump cells and/or Nernst cells, and/or combinations of two electrodes and the solid electrolyte of sensor element 114 not considered heretofore as independent cells, as temperature measuring cells 166, 168 for the temperature ascertainment. For example, in the method according to the present invention, as the result of a combined measurement of the temperature at multiple pump cells and/or Nernst cells, and/or combinations of two electrodes and the solid electrolyte not considered heretofore as independent cells, for example at temperature measuring cells 166, 168 in FIG. 1, the temperature distribution over sensor element 114 may be determined. In contrast, as described above, in the related art generally only one temperature measurement is carried out at a single Nernst cell, i.e., at only one temperature measuring point in the entire sensor element. The temperatures may thus be determined at two or more temperature measuring points 170, 172, and, for example, determined based on the ideal curve of the temperature gradient, with the aid of the two or more measured temperatures of the changed instantaneous actual temperature gradient or possibly more complex temperature distribution 158.

Thus, the deviation of the instantaneous temperature from the setpoint temperature at measuring cell 164, for example NO pump cell 142, is determinable in a first good approximation. Using the NO measuring cell temperature which is now known, the error may be corrected in various ways, which are also combinable. Thus, for example, as described above, the setpoint temperature at measuring cell 164 may be adjusted. The temperature at measuring cell 164 computed from the two or more temperature measuring points 170, 172 may be used as a control variable, for example. This variant is advantageous in particular when the temperature sensitivity of the NO signal is significantly more critical than the resulting temperature deviation at oxygen pump electrodes 130, 132.

Alternatively or additionally, a signal compensation may be carried out. Based on the ascertained deviation of the temperature at measuring cell 164, the associated signal, for example a $NO_x$ signal, in particular a current when the conventional double chamber limit current method is used, may be corrected corresponding to the known properties of the temperature dependency, for example with the aid of an offset and/or a characteristic curve slope and/or more complex compensation algorithms.

Once again alternatively or additionally, the heat supply to heating element 148 may be regulated to a compromise temperature value. This compromise temperature value may be set up to allow a moderate deviation from a setpoint temperature for multiple, which may be all, functional cells that are used for detecting the at least one property of the gas in measuring gas chamber 112. In this way, for example, also cross sensitivities of different cells may be weighted and thus taken into account.

Thus, in the method proposed according to the present invention, temperatures are detected at at least two temperature measuring points 170, 172. Alternatively or additionally, however, a separately implementable embodiment is conceivable in which, based on the above-described sensor element in one or more of the variants described above, an average temperature is ascertained over a fairly large area of sensor element 114. In turn, a regulation to this average temperature may also take place.

An extreme distortion and/or deviation of the temperature at one of the cells situated at various positions in the sensor element during regulation to only one local cell may thus be prevented. For example, as stated above, internal oxygen pump electrode 130 may be combined with reference pump electrode 140 via solid electrolyte 136 to form a temperature measuring cell. The conductivity path associated with the $R_i$ measurement then runs through solid electrolyte 136 between these electrodes 130, 140, through a large portion of sensor element 114. Other embodiments are also possible. During regulation to this internal resistance, an average temperature is thus used, and an extreme local temperature deviation over the longitudinal axis of sensor element 114 is avoided.

In another possible embodiment of the method according to the present invention and device 110 according to the present invention, measuring cell 164 may also be used in a multi-function as one of temperature measuring cells 166, 168 and/or may have all or part of the same components as a temperature measuring cell. Thus, for example, the temperature may be detected directly at measuring cell 164, for example NO pump cell 142. This may also be carried out, for example, independently from the use of multiple temperature measuring points by evaluating the noise of measuring cell 164 and/or by impressing a signal on measuring cell 164, for example NO pump cell 142; reference may be made to the procedure described above. Alternatively, this principle may be combined with multiple temperature measuring points according to the above description and according to the present invention. In order to use measuring cell 164 in a multi-function, i.e., also for measuring a temperature in addition to detecting the at least one property, for example a superimposed low-level signal may once again be impressed according to the above description, optionally also by using a digital operating method, or alternatively or additionally, the internal resistance may be estimated based on noise components in the pump voltage and/or the associated pump current. The latter procedure of determination from the noise components has the significant advantage that the very sensitive measurement of the NO decomposition current, which is typically in the nanoampere to microampere range, is not disturbed by additional polarity reversal processes, and therefore the signal quality is not adversely affected.

Another specific embodiment of the method according to the present invention lies in the use of a sensor element 114 having a hollow chamber, closed off in a gas-tight manner, according to the above description and according to the related art cited above. For example, the method may be applicable to an integrated ceramic $NO_x$ sensor. Here as well, actual measuring cell 164 or one or more of measuring cells 164 (if multiple cells are present) may once again also be used in a multi-function for a temperature measurement. For example, the NO pump electrode may cooperate with a hollow chamber electrode for a temperature measuring cell situated in the gas-tight chamber. Alternatively or additionally, a measuring cell composed of a hollow chamber electrode in the gas-tight cavity and a reference electrode, for example in an air reference, may be used in a dual function as a measuring cell and as a temperature measuring cell. Once again alternatively or additionally, a cell formed from two or more hollow chamber electrodes situated in the gas-tight chamber may be used as a temperature measuring cell. For example, the internal resistance may be ascertained from noise of a cell voltage and/or a cell current between two or more hollow chamber electrodes situated in the closed accumulation chamber. This ideally makes it possible to know the instantaneous hollow chamber temperature, which may be used for a compensation computation when there are deviations, as well as for the targeted regulation of the sensor temperature in this range. Likewise, individually or in groups, all other cells of sensor elements 114 may be used for the temperature measurement. For example, the NO pump electrode may also be combined with an air reference electrode to form a temperature measuring cell. Due to the multiphase nature of the integrated measuring principle, these measurements, depending on the properties and/or sensitivity, may be carried out in a targeted manner in the accumulation phase as well as in the initialization phase (chamber evacuation).

In another embodiment of the method according to the present invention, device 110 may include two or more heating elements 148. Thus, by use of at least two heating elements 148 inside sensor element 114, the method according to the present invention may be used not only for signal correction, but also to a great extent even for setting and regulating the optimal temperature distribution over entire sensor element 114 and/or a fairly large area of sensor element 114.

Above-described device 110 and the described method may be used in numerous already known or novel sensor configurations. For example, the device and the method, as stated, may be applied to conventional limit current $NO_x$ sensors according to FIG. 1 and/or integrated $NO_x$ sensors. Application to other types of gas sensors, for example lambda sensors, is also possible, as well as to limit current sensors and jump sensors, or combined sensors. The proposed method and proposed device 110 are particularly suited for use as an on-board diagnostic (OBD) sensor for function testing and the adaptation of a catalytic converter (SCR catalytic converter) based on selective catalytic reduction. Furthermore, in principle, other types of sensors, for example sensors for detecting other types of gas species, may be modified according to the present invention or used according to the present invention.

What is claimed is:

1. A method for detecting at least one property of a gas in a measuring gas, in particular at least one gas component of the gas, the method comprising:
    determining the at least one property with at least one electrochemical measuring cell of a sensor element by detecting temperatures at at least two different locations of the sensor element,
    wherein the sensor element has at least two temperature measuring cells,
    wherein each of the at least two temperature measuring cells has at least two electrodes and at least one solid electrolyte which connects the electrodes, and
    wherein a temperature at a location of one of the at least two temperature measuring cells is deduced from an internal resistance of one of the at least two temperature measuring cells.

2. The method of claim 1, wherein a temperature at the location of the measuring cell is deduced from the temperatures at the at least two different locations.

3. The method of claim 1, wherein the temperature at the location of the measuring cell is deduced by at least one of an extrapolation or interpolation.

4. The method of claim 2, wherein a regulation to a setpoint temperature at the location of the measuring cell is performed with at least one heating element and the temperature at the location of the measuring cell.

5. The method of claim 1, wherein at least one measured variable is detected with the aid of the measuring cell, the at least one property being determined from the measured variable, taking a correction into account, the correction being a function of at least one of a temperature at a location of the temperature measuring cell.

6. The method of claim 1, wherein a regulation of at least one temperature of the sensor element to at least one compromise temperature value is carried out with the aid of at least one heating element and the temperatures, the compromise temperature value being selected so that for multiple locations of the sensor element, for multiple functional cells of the sensor element, a predefined deviation from particular setpoint temperatures is not exceeded.

7. The method of claim 1, wherein at least one of the temperatures is detected with the aid of at least one or at least two of the temperature measuring cells.

8. The method of claim 7, wherein the temperature measuring cells include at least one of a Nernst cell and a pump cell.

9. The method of claim 7, wherein at least one of the temperature measuring cells is used in addition to the function of a temperature measurement for at least one further function, as at least one of a Nernst cell and a pump cell.

10. The method of claim 7, wherein temperatures at the location of the temperature measuring cells are detected by at least one of the following:
   modulating an application of at least one of current and voltage to the temperature measuring cells, and deducing, based on at least one of a current signal and a voltage signal, an internal resistance of the temperature measuring cells; and
   acting on the temperature measuring cells with at least one of current, voltage, and a voltage or current that results intrinsically without external impression, and deducing, based on a noise of the at least one of the current signal and the voltage signal of the temperature measuring cells, a temperature at the location of the temperature measuring cells.

11. The method of claim 10, wherein the method is used for determining a proportion of at least one of the following gas components in the gas: oxygen; nitrogen oxides; hydrocarbons; hydrogen; and ammonia.

12. A device for detecting at least one property of a gas in a measuring gas chamber, comprising:
   at least one sensor element having at least one electrochemical measuring cell and being configured to detect temperatures at at least two different locations of the sensor element, with the aid of at least one temperature measuring cell; and
   wherein the at least one sensor element includes at least one control system configured to detect at least one property of a gas in a measuring gas by determining the at least one property with at least one electrochemical measuring cell of a sensor element by detecting temperatures at at least two different locations of the sensor element.

13. The device as recited in claim 12, wherein the at least one sensor element includes at least one control system configured to detect at least one gas component of the gas in the measuring gas by determining the at least one property with at least one electrochemical measuring cell of a sensor element by detecting temperatures at at least two different locations of the sensor element.

* * * * *